(12) United States Patent
Wang

(10) Patent No.: US 11,813,348 B2
(45) Date of Patent: Nov. 14, 2023

(54) SUPRAMOLECULAR PREPARATION OF RETINOL AND DERIVATIVES THEREOF AND PREPARATION METHOD THEREFOR

(71) Applicant: PROYA COSMETICS CO., LTD., Hangzhou (CN)

(72) Inventor: Hanning Wang, Hangzhou (CN)

(73) Assignee: PROYA COSMETICS CO., LTD., Zhejiang (CN)

( * ) Notice: Subject to any disclaimer, the term of this patent is extended or adjusted under 35 U.S.C. 154(b) by 664 days.

(21) Appl. No.: 17/042,909

(22) PCT Filed: Oct. 28, 2019

(86) PCT No.: PCT/CN2019/113750
§ 371 (c)(1),
(2) Date: Sep. 28, 2020

(87) PCT Pub. No.: WO2021/017222
PCT Pub. Date: Feb. 4, 2021

(65) Prior Publication Data
US 2023/0210749 A1    Jul. 6, 2023

(30) Foreign Application Priority Data

Jul. 26, 2019   (CN) .......................... 201910681023.6

(51) Int. Cl.
*A61K 8/73*     (2006.01)
*A61K 8/67*     (2006.01)
(Continued)

(52) U.S. Cl.
CPC .............. *A61K 8/671* (2013.01); *A61K 8/345* (2013.01); *A61K 8/731* (2013.01); *A61K 8/738* (2013.01);
(Continued)

(58) Field of Classification Search
CPC ........ A61K 8/671; A61K 8/345; A61K 8/731; A61K 8/738; A61K 8/86; A61K 2008/594;
(Continued)

(56) References Cited

FOREIGN PATENT DOCUMENTS

| CN | 1625387 A   | 6/2005 |
| CN | 101641118 A | 2/2010 |

(Continued)

OTHER PUBLICATIONS

PROYA Supramolecular Retinol Serum for Face [online] retrieved on Jul. 28, 2023 from: https://www.amazon.com/PROYA-Supramolecular-Hexapeptide-1-Solution-Wrinkles/dp/B09PG4LNPL; 11 pages (Year: 2023).*

(Continued)

*Primary Examiner* — Ernst V Arnold
(74) *Attorney, Agent, or Firm* — ArentFox Schiff LLP

(57) ABSTRACT

The present disclosure relates to a supramolecular preparation of retinol and derivatives thereof and a preparation method therefor, wherein the supramolecular preparation consists of following components in percentage by mass: 3.00-25.0% of retinol and derivatives thereof, 36.5-91.0% of hydroxypropyl γ-cyclodextrin, 4.00-32.0% of hydroxypropyl methylcellulose stearoxy ether, and 2.00-8.0% of PEG/PPG/polybutylene glycol-8/5/3 glycerin, wherein the mass ratio of the PEG/PPG/polybutylene glycol-8/5/3 glycerin to the hydroxypropyl methylcellulose stearoxy ether is 1:2-4. The supramolecular preparation of retinol and derivatives thereof obtained in the present disclosure has the advantages such as good stability, high solubility, low irritation, and good anti-wrinkle effect.

20 Claims, 1 Drawing Sheet

(51) Int. Cl.
*A61K 8/34* (2006.01)
*A61K 8/86* (2006.01)
*A61Q 19/08* (2006.01)

(52) U.S. Cl.
CPC ............... *A61K 8/86* (2013.01); *A61Q 19/08* (2013.01); *A61K 2800/594* (2013.01); *A61K 2800/805* (2013.01)

(58) Field of Classification Search
CPC ...... A61K 2800/805; A61K 8/67; A61K 8/73; A61K 2800/72; A61Q 19/08; A61Q 19/00
See application file for complete search history.

(56) References Cited

FOREIGN PATENT DOCUMENTS

| CN | 103476432 A | 12/2013 | | |
|---|---|---|---|---|
| CN | 103987391 A | 8/2014 | | |
| CN | 108026131 A | 5/2018 | | |
| WO | WO-2013142249 A1 | * | 9/2013 | ............. A61K 31/07 |

OTHER PUBLICATIONS

International Search Report for International Application No. PCT/CN2019/113750, dated Apr. 26, 2020, ISA/CN.

Meng, Fanyue, "Cyclodextrin Supramolecular Delivery System Improves the Stability of Vitamin A Palmitate", Medicine & Public Health, China Master's Theses Full-Text Database), Mar. 15, 2018, No. 03.

H. Aldawsari et al. "Combined use of cyclodextrins and hydroxypropylmethylcellulose stearoxy ether (Sangelose®) for the preparation of orally disintegrating tablets of type-2 antidiabetes agent glimepiride", J. Incl. Phenom. Macrocycl. Chem., Feb. 6, 2014, vol. 80.

* cited by examiner

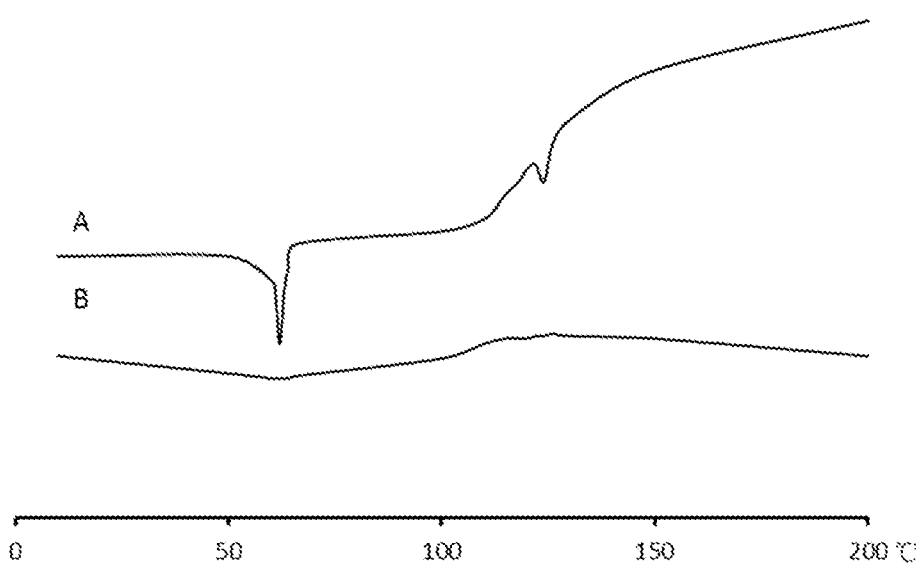

SUPRAMOLECULAR PREPARATION OF RETINOL AND DERIVATIVES THEREOF AND PREPARATION METHOD THEREFOR

CROSS-REFERENCE TO RELATED APPLICATION

This application is a 371 U.S. national stage of PCT/CN2019/113750, filed Oct. 28, 2019, which claims priority of Chinese patent application number 201910681023.6, filed on Jul. 26, 2019, the contents of each of which are incorporated herein by reference in entirety.

The present disclosure relates to the technical field of preparation of skin care products, in particular to a supramolecular preparation of retinol and derivatives thereof and a preparation method therefor.

BACKGROUND ART

Retinol has a long history for use in the treatment of skin roughness and keratinization, and has been favored by consumers as a well-established effective anti-aging component for skin in recent years. However, the special physicochemical properties of retinol limit its applications: retinol is easy to be deactivated under the conditions of light, heat and oxygen, has a small molecular weight and high permeability, and may cause irritation problems such as skin redness and swelling, and hot pain when being improperly used. The retinol derivatives obtained by chemical structure modification can have improved stability and reduced irritation to a certain extent, but corresponding efficacy will be weakened to different degrees. Besides, methods for solving the problems of application of retinol and its derivatives to cosmetics further include lipidization, micro-acupuncture, addition of a light protectant, and design of a special package and so on, but there are still problems such as complicated preparation, and low protection efficiency.

Supramolecule refers to a highly complex and regular organization formed by spontaneous assembling of two or more compound molecules through intermolecular non-covalent bond interactions. Generally, intermolecular forces are weak interactions, mainly including hydrogen bonds, electrostatic interactions, stacking interactions, hydrophobic/hydrophilic interactions, coordination bonds and so on, and the intermolecular forces can be superposed to a certain extent, the synergistic effect renders a stronger binding force, and a supramolecule assembled by means of such a force can improve solubility, stability and permeability of active materials in the premise of maintaining the original activity of the active materials, and even obtain special properties completely different from the original molecules.

Cyclodextrin is a kind of macrocyclic molecules of natural origin. Its internally hydrophobic and externally hydrophilic structure determines its special position in supramolecular chemistry. Cyclodextrin can form supramolecules with coordination compounds utilizing the hydrophobic/hydrophilic interaction and cavitation, and the application range can be expanded by structural modification. At present, there are more researches on cyclodextrin supramolecules, products of cyclodextrin inclusion compounds of retinol are already available on the market, but the supramolecular treatment of retinol only by taking cyclodextrin as a material still has some shortcomings, for example, it can only be dispersed in water to form a suspension, layering will occur after placement for about 1 week, and the loading capacity for the retinol is limited, then sufficient protection effect cannot be provided by only relying on cyclodextrin under the condition of high loading capacity, and there are problems of light and thermal stability after long-term placement. In the present disclosure, the supramolecular preparation is formed by hydrophobic/hydrophilic interaction of cyclodextrin and association of a supramolecule associate agent by intermolecular interaction, which has a stable structure and stable property, and slow release capacity, thereby solving the problems of stability and irritation in the application of retinol and derivatives thereof, and further playing a better role in resisting wrinkles.

SUMMARY

The technical problem to be solved by the present disclosure is to provide a supramolecular preparation of retinol and derivatives thereof with good stability and a preparation method therefor.

The present disclosure relates to a supramolecular preparation of retinol and derivatives thereof, consisting of following components in percentage by mass: 3.00-25.0% of retinol and derivatives thereof, 36.5-91.0% of hydroxypropyl γ-cyclodextrin, 4.00-32.0% of hydroxypropyl methylcellulose stearoxy ether, and 2.00-8.0% of PEG/PPG/polybutylene glycol-8/5/3 glycerin, wherein the mass ratio of the PEG/PPG/polybutylene glycol-8/5/3 glycerin to the hydroxypropyl methylcellulose stearoxy ether is 1:2-4.

In one or more embodiments, the retinol and derivatives thereof include at least one of retinol, retinyl propionate, retinyl retinoate, retinyl linoleate, retinyl acetate, retinyl palmitate, retinal, hydroxypinacolone retinoate.

In one or more embodiments, the supramolecular preparation of retinol and derivatives thereof consists of following components in percentage by mass: 5-20% of retinol and derivatives thereof, 50-80% of hydroxypropyl γ-cyclodextrin, 8.00-25.0% of hydroxypropyl methylcellulose stearoxy ether, and 3.00-7.0% of PEG/PPG/polybutylene glycol-8/5/3 glycerin.

In one or more embodiments, the supramolecular preparation of retinol and derivatives thereof consists of following components in percentage by mass: 6-15% of retinol and derivatives thereof, 60-75% of hydroxypropyl γ-cyclodextrin, 10.00-20.0% of hydroxypropyl methylcellulose stearoxy ether, and 4.00-6.0% of PEG/PPG/polybutylene glycol-8/5/3 glycerin.

In one or more embodiments, the supramolecular preparation of retinol and derivatives thereof consists of following components in percentage by mass: 8-12% of retinol and derivatives thereof, 65-72% of hydroxypropyl γ-cyclodextrin, 12.00-18.0% of hydroxypropyl methylcellulose stearoxy ether, and 4.5-5.5% of PEG/PPG/polybutylene glycol-8/5/3 glycerin.

In one or more embodiments, the supramolecular preparation of retinol and derivatives thereof consists of following components in percentage by mass: 10% of retinol and derivatives thereof, 70% of hydroxypropyl γ-cyclodextrin, 15% of hydroxypropyl methylcellulose stearoxy ether, and 5% of PEG/PPG/polybutylene glycol-8/5/3 glycerin.

In one or more embodiments, the mass ratio of the PEG/PPG/polybutylene glycol-8/5/3 glycerin to the hydroxypropyl methylcellulose stearoxy ether is 1:2.2-3.8 in the supramolecular preparation of retinol and derivatives thereof.

In one or more embodiments, the mass ratio of the PEG/PPG/polybutylene glycol-8/5/3 glycerin to the hydroxypropyl methylcellulose stearoxy ether is 1:2.4-3.6 in the supramolecular preparation of retinol and derivatives thereof.

In one or more embodiments, the mass ratio of the PEG/PPG/polybutylene glycol-8/5/3 glycerin to the hydroxypropyl methylcellulose stearoxy ether is 1:2.6-3.4 in the supramolecular preparation of retinol and derivatives thereof.

In one or more embodiments, the mass ratio of the PEG/PPG/polybutylene glycol-8/5/3 glycerin to the hydroxypropyl methylcellulose stearoxy ether is 1:2.8-3.2 in the supramolecular preparation of retinol and derivatives thereof.

In one or more embodiments, the mass ratio of the PEG/PPG/polybutylene glycol-8/5/3 glycerin to the hydroxypropyl methylcellulose stearoxy ether is 1:3 in the supramolecular preparation of retinol and derivatives thereof.

The present disclosure relates to a cosmetic composition including the supramolecular preparation of retinol and derivatives thereof as described herein.

In one or more embodiments, the cosmetic composition is an emollient, soothing oil, lotion cream, day cream, night cream, eye cream, UV protection product, anti-wrinkle product, gel, mask, balm, powder or sunscreen product.

The present disclosure relates to use of the supramolecular preparation of retinol and derivatives thereof described herein or the cosmetic composition described herein in preparation of an anti-wrinkle product.

In one or more embodiments, the anti-wrinkle product is eye cream, lotion cream, day cream or night cream.

A method for preparing a supramolecular preparation of retinol and derivatives thereof, adopting following steps:

A. weighing 3.00-25.0% of retinol and derivatives thereof, 36.5-91.0% of hydroxypropyl γ-cyclodextrin, 4.00-32.0% of hydroxypropyl methylcellulose stearoxy ether, and 2.00-8.0% of PEG/PPG/polybutylene glycol-8/5/3 glycerin in percentage by mass, wherein a mass ratio of the PEG/PPG/polybutylene glycol-8/5/3 glycerin to the hydroxypropyl methylcellulose stearoxy ether is 1:2-4;

B. weighing an appropriate amount of deionized water, mixing the hydroxypropyl γ-cyclodextrin and the deionized water in a mass ratio of 1:3, and stirring them with an agitator at a rotational speed of 500-800 rpm until the hydroxypropyl γ-cyclodextrin is completely dissolved to obtain an aqueous hydroxypropyl γ-cyclodextrin solution;

C. weighing an appropriate amount of ethanol, dissolving the retinol and derivatives thereof in the ethanol in a mass ratio of 1:2-10, mixing them uniformly, and afterwards adding the mixture dropwise into the aqueous hydroxypropyl γ-cyclodextrin solution obtained in step B at a rate of 5-20 ml per minute, and meanwhile keeping stirring the aqueous hydroxypropyl γ-cyclodextrin solution at a rotational speed of 500-800 rpm to obtain a mixed solution;

D. adding PEG/PPG/polybutylene glycol-8/5/3 glycerin and hydroxypropyl methylcellulose stearoxy ether in sequence to the mixed solution obtained in step C, and after stirring them uniformly, loading the resultant in a sand mill to perform cyclical milling for 10-20 times, wherein the rotational speed is controlled at 3000-3500 rpm, and the temperature is not higher than 40° C., to obtain a pre-prepared liquid after completing the milling; and E. spray-drying the pre-prepared liquid obtained in step D under nitrogen protection using a spray dryer, wherein an air inlet temperature is controlled at 100-120° C., and a feed rate is controlled at 10-20 mL/min, and collecting a spray-dried product to obtain a supramolecular preparation of retinol and derivatives thereof.

BRIEF DESCRIPTION OF DRAWINGS

In order to more clearly illustrate technical solutions of embodiments of the present disclosure, drawings which need to be used in the embodiments will be introduced briefly below, and it should be understood that the drawings below merely show some embodiments of the present disclosure, and therefore should not be considered as limitation on the scope. A person ordinarily skilled in the art still could obtain other relevant drawings according to these drawings without inventive effort.

FIG. 1 is a differential scanning calorimetry map for supramolecular structure confirmation.

DETAILED DESCRIPTION OF EMBODIMENTS

In order to make the objects, technical solutions and advantages of the embodiments of the present disclosure clearer, the technical solutions in the embodiments of the present disclosure will be described clearly and completely below. If no specific conditions are specified in the embodiments, they are carried out under normal conditions or conditions recommended by the manufacturer. If the manufacturers of reagents or apparatuses used are not specified, they are conventional products commercially available.

Unless otherwise defined herein, scientific and technical terms used in the present disclosure should have meanings that are commonly understood by those ordinarily skilled in the art. Exemplary methods and materials are described below, but methods and materials similar or equivalent to those described herein can also be used in the practice or testing of the present disclosure.

The agitator used in the present disclosure is R20 agitator of IKA company; the sand mill used in the present disclosure is a nano-scale circulating sand mill Zeta RS, manufactured by German NETZSCH company, the milling medium used is zirconia beads, and a mean particle size of the milling medium is 500 μm; the spray dryer in the present disclosure is from Swiss BUCHI company, model B-290, with a B-295 organic solvent recovery device.

As used herein, the term "retinol and derivatives thereof" refer to retinol and/or derivatives thereof, which may be retinol, or derivatives thereof, or a combination of retinol and derivatives thereof.

The retinol and derivatives thereof described in the present disclosure are one of retinol, retinyl propionate, retinyl retinoate, retinyl linoleate, retinyl acetate, retinyl palmitate, retinal, hydroxypinacolone retinoate, or a mixture thereof in any ratio, and the above names of retinol and derivatives thereof are all standard INCI names in the Chinese *Catalogue of Already-used Cosmetic Raw Materials* (2015).

The hydroxypropyl γ-cyclodextrin in the present disclosure, with CAS No. 128446-34-4, is one of the derivatives of γ-cyclodextrin, of which the INCI name is hydroxypropylcyclodextrin, with the serial number 05228 in the *Catalogue of Already-used Cosmetic Raw Materials* (2015), and compared with other configurations, the hydroxypropyl γ-cyclodextrin has a larger internal cavity, and also has further improved solubility after being modified by hydroxypropyl. Hydroxypropyl γ-cyclodextrin has an internally hydrophobic and externally hydrophilic macrocyclic molecular structure, and includes the ligand molecules by cavitation. A commercially available product of hydroxypropyl γ-cyclodextrin may be available from Shandong Binzhou Zhiyuan Biotechnology Co., Ltd.

The supramolecular associate agent described in the present disclosure consists of hydroxypropyl methylcellulose stearoxy ether and PEG/PPG/polybutylene glycol-8/5/3 glycerin. The PEG/PPG/polybutylene glycol-8/5/3 glycerin has oil-water amphiphilic properties, which can help to associate the lipophilic methoxyl group on a linear chain of hydroxypropyl methylcellulose stearoxy ether and hydrophilic hydroxyl of the outer cavity of the hydroxypropyl γ-cyclodextrin by an intermolecular force, so as to form a stable supramolecular structure.

The serial number of the PEG/PPG/polybutylene glycol-8/5/3 glycerin described in the present disclosure is 00432 in the Chinese *Catalogue of Already-used Cosmetic Raw Materials* (2015), and the commercially available product of PEG/PPG/polybutylene glycol-8/5/3 glycerin may be available from Japanese NOF company, with the brand number WILBRIDE S-753.

The hydroxypropyl methylcellulose stearoxy ether described in the present disclosure, with the serial number 05230 in the Chinese *Catalogue of Already-used Cosmetic Raw Materials* (2015), is a kind of hydrophobic derivative of hydroxypropyl methylcellulose, in which the methoxyl and hydroxyl are distributed uniformly along the cellulose chain. The commercially available product of hydroxypropyl methylcellulose stearoxy ether may be available from Japanese DAIDO Chemical Corporation, with the brand number Sangelose 60L, Sangelose 90L.

The deionized water used in the present disclosure should have the conductivity below 10 micromho. The ethanol used in the present disclosure is analytically pure.

In the present disclosure, the hydroxypropyl γ-cyclodextrin and the supramolecular associate agent are used to carry out supramolecular treatment on the retinol and derivatives thereof, and the supramolecular preparation formed has a stable structure and stable property, with improved light and thermal stabilities, and has slow release capability, thus effectively alleviating the irritation caused by direct contact of high concentration of retinol and derivatives thereof with skin, which is beneficial to the mild and sustained play of anti-wrinkle effect of the retinol and derivatives thereof.

Example 1: A supramolecular preparation of retinol and derivatives thereof and a preparation method therefor, adopting following steps:
   A. weighing 10.0% of retinol, 70.0% of hydroxypropyl γ-cyclodextrin, 15.0% of hydroxypropyl methylcellulose stearoxy ether, and 5.00% of PEG/PPG/polybutylene glycol-8/5/3 glycerin in percentage by mass;
   B. weighing an appropriate amount of deionized water, mixing the hydroxypropyl γ-cyclodextrin and the deionized water in a mass ratio of 1:3, and stirring them with an agitator at a rotational speed of 500-800 rpm until the hydroxypropyl γ-cyclodextrin was completely dissolved to obtain an aqueous hydroxypropyl γ-cyclodextrin solution;
   C. weighing an appropriate amount of ethanol, dissolving the retinol and derivatives thereof in the ethanol in a mass ratio of 1:2-10, mixing them uniformly, and afterwards adding the mixture dropwise into the aqueous hydroxypropyl γ-cyclodextrin solution obtained in step B at a rate of 5-20 ml per minute, and meanwhile keeping stirring the aqueous hydroxypropyl γ-cyclodextrin solution at a rotational speed of 500-800 rpm to obtain a mixed solution;
   D. adding PEG/PPG/polybutylene glycol-8/5/3 glycerin and hydroxypropyl methylcellulose stearoxy ether in sequence to the mixed solution obtained in step C, and after stirring them uniformly, loading the resultant in a sand mill to perform cyclical milling for 10-20 times, wherein the rotational speed was controlled at 3000-3500 rpm, and the temperature was not higher than 40° C., to obtain a pre-prepared liquid after completing the milling; and
   E. spray-drying the pre-prepared liquid obtained in step D under nitrogen protection using a spray dryer, wherein an air inlet temperature was controlled at 100-120° C., and a feed rate was controlled at 10-20 mL/min, and collecting a spray-dried product, to obtain a supramolecular preparation of retinol and derivatives thereof.

Example 2: A supramolecular preparation of retinol and derivatives thereof and a preparation method therefor, adopting following steps:
   A. weighing 8.50% of retinol, 15.00% of retinyl palmitate, 36.5% of hydroxypropyl γ-cyclodextrin, 32.00% of hydroxypropyl methylcellulose stearoxy ether, and 8.00% of PEG/PPG/polybutylene glycol-8/5/3 glycerin in percentage by mass;
   B. weighing an appropriate amount of deionized water, mixing the hydroxypropyl γ-cyclodextrin and the deionized water in a mass ratio of 1:3, and stirring them with an agitator at a rotational speed of 500-800 rpm until the hydroxypropyl γ-cyclodextrin was completely dissolved to obtain an aqueous hydroxypropyl γ-cyclodextrin solution;
   C. weighing an appropriate amount of ethanol, dissolving the retinol and derivatives thereof in the ethanol in a mass ratio of 1:2-10, mixing them uniformly, and afterwards adding the mixture dropwise into the aqueous hydroxypropyl γ-cyclodextrin solution obtained in step B at a rate of 5-20 ml per minute, and meanwhile keeping stirring the aqueous hydroxypropyl γ-cyclodextrin solution at a rotational speed of 500-800 rpm to obtain a mixed solution;
   D. adding PEG/PPG/polybutylene glycol-8/5/3 glycerin and hydroxypropyl methylcellulose stearoxy ether in sequence to the mixed solution obtained in step C, and after stirring them uniformly, loading the resultant in a sand mill to perform cyclical milling for 10-20 times, wherein the rotational speed was controlled at 3000-3500 rpm, and the temperature was not higher than 40° C., to obtain a pre-prepared liquid after completing the milling; and
   E. spray-drying the pre-prepared liquid obtained in step D under nitrogen protection using a spray dryer, wherein an air inlet temperature was controlled at 100-120° C., and a feed rate was controlled at 10-20 mL/min, and collecting a spray-dried product, to obtain a supramolecular preparation of retinol and derivatives thereof.

Example 3: A supramolecular preparation of retinol and derivatives thereof and a preparation method therefor, adopting following steps:
   A. weighing 2.00% of retinyl palmitate, 1.00% of retinal, 91.0% of hydroxypropyl γ-cyclodextrin, 4.00% of hydroxypropyl methylcellulose stearoxy ether, and 2.00% of PEG/PPG/polybutylene glycol-8/5/3 glycerin in percentage by mass;
   B. weighing an appropriate amount of deionized water, mixing the hydroxypropyl γ-cyclodextrin and the deionized water in a mass ratio of 1:3, and stirring them with an agitator at a rotational speed of 500-800 rpm until the hydroxypropyl γ-cyclodextrin was completely dissolved to obtain an aqueous hydroxypropyl γ-cyclodextrin solution;

C. weighing an appropriate amount of ethanol, dissolving the retinol and derivatives thereof in the ethanol in a mass ratio of 1:2-10, mixing them uniformly, and afterwards adding the mixture dropwise into the aqueous hydroxypropyl γ-cyclodextrin solution obtained in step B at a rate of 5-20 ml per minute, and meanwhile keeping stirring the aqueous hydroxypropyl γ-cyclodextrin solution at a rotational speed of 500-800 rpm to obtain a mixed solution;

D. adding PEG/PPG/polybutylene glycol-8/5/3 glycerin and hydroxypropyl methylcellulose stearoxy ether in sequence to the mixed solution obtained in step C, and after stirring them uniformly, loading the resultant in a sand mill to perform cyclical milling for 10-20 times, wherein the rotational speed was controlled at 3000-3500 rpm, and the temperature was not higher than 40° C., to obtain a pre-prepared liquid after completing the milling; and E. spray-drying the pre-prepared liquid obtained in step D under nitrogen protection using a spray dryer, wherein an air inlet temperature was controlled at 100-120° C., and a feed rate was controlled at 10-20 mL/min, and collecting a spray-dried product, to obtain a supramolecular preparation of retinol and derivatives thereof.

Example 4: A supramolecular preparation of retinol and derivatives thereof and a preparation method therefor, adopting following steps:

A. weighing 25.0% of retinol, 49.0% of hydroxypropyl γ-cyclodextrin, 20.0% of hydroxypropyl methylcellulose stearoxy ether, and 6.00% of PEG/PPG/polybutylene glycol-8/5/3 glycerin in percentage by mass;

B. weighing an appropriate amount of deionized water, mixing the hydroxypropyl γ-cyclodextrin and the deionized water in a mass ratio of 1:3, and stirring them with an agitator at a rotational speed of 500-800 rpm until the hydroxypropyl γ-cyclodextrin was completely dissolved to obtain an aqueous hydroxypropyl γ-cyclodextrin solution;

C. weighing an appropriate amount of ethanol, dissolving the retinol and derivatives thereof in the ethanol in a mass ratio of 1:2-10, mixing them uniformly, and afterwards adding the mixture dropwise into the aqueous hydroxypropyl γ-cyclodextrin solution obtained in step B at a rate of 5-20 ml per minute, and meanwhile keeping stirring the aqueous hydroxypropyl γ-cyclodextrin solution at a rotational speed of 500-800 rpm to obtain a mixed solution;

D. adding PEG/PPG/polybutylene glycol-8/5/3 glycerin and hydroxypropyl methylcellulose stearoxy ether in sequence to the mixed solution obtained in step C, and after stirring them uniformly, loading the resultant in a sand mill to perform cyclical milling for 10-20 times, wherein the rotational speed was controlled at 3000-3500 rpm, and the temperature was not higher than 40° C., to obtain a pre-prepared liquid after completing the milling; and E. spray-drying the pre-prepared liquid obtained in step D under nitrogen protection using a spray dryer, wherein an air inlet temperature was controlled at 100-120° C., and a feed rate was controlled at 10-20 mL/min, and collecting a spray-dried product, to obtain a supramolecular preparation of retinol and derivatives thereof.

Example 5: A supramolecular preparation of retinol and derivatives thereof and a preparation method therefor, adopting following steps:

A. weighing 7.50% of retinol, 3.00% of retinyl propionate, 6.00% of retinyl acetate, 60.0% of hydroxypropyl γ-cyclodextrin, 16.0% of hydroxypropyl methylcellulose stearoxy ether, and 7.50% of PEG/PPG/polybutylene glycol-8/5/3 glycerin in percentage by mass;

B. weighing an appropriate amount of deionized water, mixing the hydroxypropyl γ-cyclodextrin and the deionized water in a mass ratio of 1:3, and stirring them with an agitator at a rotational speed of 500-800 rpm until the hydroxypropyl γ-cyclodextrin was completely dissolved to obtain an aqueous hydroxypropyl γ-cyclodextrin solution;

C. weighing an appropriate amount of ethanol, dissolving the retinol and derivatives thereof in the ethanol in a mass ratio of 1:2-10, mixing them uniformly, and afterwards adding the mixture dropwise into the aqueous hydroxypropyl γ-cyclodextrin solution obtained in step B at a rate of 5-20 ml per minute, and meanwhile keeping stirring the aqueous hydroxypropyl γ-cyclodextrin solution at a rotational speed of 500-800 rpm to obtain a mixed solution;

D. adding PEG/PPG/polybutylene glycol-8/5/3 glycerin and hydroxypropyl methylcellulose stearoxy ether in sequence to the mixed solution obtained in step C, and after stirring them uniformly, loading the resultant in a sand mill to perform cyclical milling for 10-20 times, wherein the rotational speed was controlled at 3000-3500 rpm, and the temperature was not higher than 40° C., to obtain a pre-prepared liquid after completing the milling; and E. spray-drying the pre-prepared liquid obtained in step D under nitrogen protection using a spray dryer, wherein an air inlet temperature was controlled at 100-120° C., and a feed rate was controlled at 10-20 mL/min, and collecting a spray-dried product, to obtain a supramolecular preparation of retinol and derivatives thereof.

In order to demonstrate the beneficial effects of the supramolecular preparation of the retinol and derivatives thereof prepared in the present disclosure, the following experiments were conducted.

1. Supramolecular Structure Confirmation

A retinol pure product was chosen as a sample A; the supramolecular preparation prepared in Example 1 (wherein the mass percentage of retinol was 10%) was chosen as a sample B; and specific compositions and the preparation method are as shown in Table 1.

TABLE 1

Compositions of Experimental Samples for Supramolecular Structure Confirmation

| Samples | Retinol | Hydroxypropyl γ-cyclodextrin | Hydroxypropyl Methylcellulose Stearoxy Ether | PEG/PPG/ Polybutylene Glycol- 8/5/3 Glycerin |
|---|---|---|---|---|
| A | 100 | / | / | / |
| B | 10.0 | 70.0 | 15.00 | 5.0 |

The formation of the supramolecule was confirmed by differential scanning calorimetry, the temperature was raised at a speed of 10° C./min, and scanning was carried out at a temperature range of 10-200° C., with the result as shown in FIG. 1. It can be seen from FIG. 1 that the sample A has a characteristic peak in the vicinity of both 60° C. and 125° C., which is related to the melting temperature and the decomposition temperature of retinol, while the curve of the sample B having undergone the supramolecular treatment is smooth, and the retinol characteristic peak disappears, indicating that a new stable structure is formed with the hydroxypropyl γ-cyclodextrin and the supramolecular associate agent, which can characterize the formation of the supramolecular structure thereof.

Therefore, the supramolecular preparation of retinol and derivatives thereof prepared in the present disclosure can form a supramolecular structure after the supramolecular treatment on the retinol by specific materials and ratios.

2. Stability Test

The supramolecular preparation prepared in Example 1 (wherein the mass percentage of retinol is 10%) was chosen as a sample A, and synchronously, preparations prepared by the same method and having the same mass percentage of retinol as the sample A, but without the addition of hydroxypropyl methylcellulose stearoxy ether or PEG/PPG/polybutylene glycol-8/5/3 glycerin were chosen as samples B and C, respectively, and the preparation without the addition of supramolecular associate agent was chosen as a sample D. Specific compositions are as shown in Table 2:

TABLE 2

Compositions and Ratios of Samples for Stability Experiment

| Samples | Retinol | Hydroxypropyl γ-cyclodextrin | Hydroxypropyl Methylcellulose Stearoxy Ether | PEG/PPG/ Polybutylene Glycol- 8/5/3 Glycerin |
|---|---|---|---|---|
| A | 10.0 | 70.0 | 15.00 | 5.0 |
| B | 10.0 | 75.0 | 15.00 | / |
| C | 10.0 | 85.0 | / | 5.0 |
| D | 10.0 | 90.0 | / | / |

The above samples were placed under 25° C., 40° C. and light condition to carry out the stability experiment, respectively, and the content of retinol was measured by HPLC method at 1, 2, 3, 4 weeks. For a specific method, methanol was taken as a mobile phase, Eclipse XDB-C18 was chosen as a chromatographic column, 5 μm, 150 mm*4.6 mm, or other suitable chromatographic columns were chosen, wherein the column temperature was 30° C., the flow rate was 0.8 mL/min, the detection wavelength was 320 nm, and the sample amount was 5 μL. The retention rate of retinol was calculated according to the content measurement results, and the results are as shown in Table 3.

TABLE 3

Results of Stability Test

| Samples | Retention Rate of Retinol (%) | | | Observation Time |
|---|---|---|---|---|
| | 25° C. | 40° C. | Lighting | |
| A | 99.93 | 98.61 | 98.98 | 1 week |
| | 99.82 | 97.43 | 97.74 | 2 weeks |
| | 99.67 | 96.32 | 96.87 | 3 weeks |
| | 99.74 | 95.08 | 96.10 | 4 weeks |
| B | 99.82 | 98.20 | 97.44 | 1 week |
| | 99.69 | 96.74 | 95.15 | 2 weeks |
| | 98.53 | 93.28 | 92.59 | 3 weeks |
| | 98.25 | 88.43 | 89.26 | 4 weeks |
| C | 99.77 | 97.26 | 98.53 | 1 week |
| | 99.23 | 94.23 | 97.34 | 2 weeks |
| | 98.96 | 90.16 | 95.41 | 3 weeks |
| | 98.69 | 80.66 | 92.06 | 4 weeks |

TABLE 3-continued

Results of Stability Test

| Samples | Retention Rate of Retinol (%) | | | Observation Time |
|---|---|---|---|---|
| | 25° C. | 40° C. | Lighting | |
| D | 98.24 | 90.17 | 90.32 | 1 week |
| | 95.83 | 87.55 | 86.28 | 2 weeks |
| | 92.09 | 82.76 | 74.35 | 3 weeks |
| | 85.65 | 75.11 | 68.06 | 4 weeks |

It can be seen from the table above that after the 4-week stability test, the sample A has a retention ratio of retinol higher than 95% under 25° C., 40° C. and light condition, while the sample B has slightly declined light and thermal stability results, and has the retention rate of retinol less than 90%, the light stability of the sample C is declined more obviously, and the retention ratio of retinol under light condition is only 80.66%, the light and thermal stabilities of the sample D are neither good, and the retention ratio of retinol under 40° C. and light condition was less than 80%. This indicates that both light and thermal stabilities are improved after the retinol has undergone the supramolecular treatment with the supramolecular associate agent in a specific proportion. Therefore, the supramolecular treatment technology provided in the present disclosure has the effect of stabilizing and protecting the retinol and derivatives thereof, and can improve the light and thermal stabilities thereof.

3. Irritation Test 35 volunteers of 18-60 years old were chosen to carry out irritation test with reference to Safety and Technical Standards for Cosmetics 2015-Human Skin Patch Test.

The mass percentage of retinol added to the night cream was 0.30%, and the supramolecular preparation prepared in Example 1 (wherein the mass percentage of retinol was 10%) and the retinol pure product were added to the night cream as sample A and sample B, respectively. Compositions of the night cream formulation are as shown in Table 4.

TABLE 4

Compositions of Irritation Test Sample Night Cream

| Names of Components | Mass Percentage % | |
|---|---|---|
| | Sample A | Sample B |
| deionized water | To 100 | To 100 |
| cetearyl olivate/sorbitan olivate | 1.50 | 1.50 |
| glycerin | 3.00 | 3.00 |
| xanthan gum | 0.30 | 0.30 |
| acrylate/C10-30 alkyl acrylate cross-linked copolymer | 0.20 | 0.20 |
| trisodium ethylenediamine disuccinate (37%) | 0.30 | 0.30 |
| cetyl palmitate/sorbitan palmitate/sorbitan olivate | 1.00 | 1.00 |
| ethylhexyl olivate | 2.00 | 2.00 |
| cetearyl alcohol | 1.50 | 1.50 |
| dicaprylyl carbonate | 2.00 | 2.00 |
| isodecyl pivalate | 5.00 | 5.00 |
| supramolecular preparation prepared according to Example 1 (wherein the mass percentage of retinol is 10%) | 3.00 | / |
| retinol | | 0.30 |
| sodium hydroxide | 0.09 | 0.09 |

The samples A and B were added into Finn Chambers, then the Finn Chambers added with the samples were applied onto the back of subjects with a non-irritating adhesive tape, and lightly pressed with palm to uniformly apply the Finn Chambers onto the skin for 24 H continuously; the Finn Chambers of test substances were removed, the test substance residue on test sites were slightly wiped with a wet absorbent cotton ball, and after 0.5 H, skin reaction was observed after the indentation disappeared. If the result was negative, observation was made again after the patch was removed for 24 H. The reaction results were recorded according to a graded scale, and effective results are as shown in Table 5.

mainly performed indoor activities during the test period, avoiding long-term unprotected exposure to sunlight.

The canthi of the volunteers were selected as test sites, the follow-ups were respectively carried out before the use and after the use for 2 weeks and 4 weeks, 3 times in total, the follow-ups required to be carried out after the volunteers cleaned their face, the quantity of wrinkles, the average depth of total wrinkles and the ratio of the wrinkle area were measured by the same person by adopting PROMIS LITE wrinkle measuring instrument of German LMI Technologies company, and results are as shown in Table 6.

TABLE 5

Test Results of Irritation Test (the number of effective test volunteers was 31)

| Samples | Observation Time | Grade 0 | Grade 1 | Grade 2 | Grade 3 | Grade 4 | Test Results | Conclusions |
|---|---|---|---|---|---|---|---|---|
| A | 0.5 h | 30 | 1$^{(22)}$ | 0 | 0 | 0 | 1 of 31 people had adverse skin reactions | No adverse skin reaction to human body |
|   | 24 h | 31 | 0 | 0 | 0 | 0 | | |
| B | 0.5 h | 28 | 0 | 3$^{(4, 16, 22,)}$ | 0 | 0 | 8 of 31 people had adverse skin reactions | Adverse skin reaction to human body |
|   | 24 h | 23 | 4$^{(2, 7, 16, 22)}$ | 3$^{(11, 23, 31)}$ | 1$^{(29)}$ | 0 | | |
| Finn Chamber Blank | 0.5 h | 31 | 0 | 0 | 0 | 0 | 0 of 31 people had adverse skin reactions | No adverse skin reaction to human body |
|   | 24 h | 31 | 0 | 0 | 0 | 0 | | |

Notes:
1$^{(22)}$ means that the number of people having adverse reaction is 1, and the serial number of corresponding subject is 22.

As can be seen from the above table, in the case that the retinol was added to the night cream in a mass percentage of 0.3%, the supramolecular preparation prepared in the present disclosure had no adverse reaction on the skin of human body, and the adverse reaction of the retinol which was not subjected to supramolecular treatment was relatively serious. This indicates that the supramolecular treatment can reduce the irritation of retinol and derivatives thereof, and avoid the irritation problems such as redness and swelling, hot pain and desquamation of skin caused by high concentrations of retinol and derivatives thereof.

4. Experiment for Efficacy on Human Body

In order to further prove the efficacy of the supramolecular preparation of retinol and derivatives thereof prepared in the present disclosure, a test for efficacy on human body was carried out, and specific steps are as follows: selecting 15 female volunteers who were not in preconception, lactation and pregnancy stages and aged 35-50 years, with the wrinkle grades of the left and right canthi being consistent and all greater than 1, randomly dividing the left and right sides into an experiment side and a control side, wherein the night cream added with 3% of the supramolecular preparation of retinol and derivatives thereof prepared in Example 1 (See the sample A in Table 4 for the formula) was used for the experiment side, and blank night cream without the addition of retinol was used for the control side.

In the experiment, volunteers were required to use the night creams every night and ensure that the volunteers

TABLE 6

Experiment Results of Efficacy on Human Body

| Groups | Quantity of Wrinkles | Average Depth of Total Wrinkles/μm | Ratio of Wrinkle Area % | Test Time/ week |
|---|---|---|---|---|
| Experiment Group | 18.3 | 93.0 | 14.8 | 0 |
|   | 17.6 | 87.5 | 13.3 | 2 |
|   | 15.0 | 77.6 | 11.6 | 4 |
| Control Group | 18.6 | 92.8 | 14.9 | 0 |
|   | 18.4 | 93.1 | 14.6 | 2 |
|   | 17.8 | 91.0 | 14.8 | 4 |

As can be seen from the above table, in the follow-ups of 2 and 4 weeks, the quantity of wrinkles in the experiment group was reduced by 4.35% and 15.73%, respectively, the average depth of total wrinkles was reduced by 6.02% and 14.72%, respectively, and the average ratio of wrinkle area was reduced by 8.90% and 21.62%, respectively. Therefore, the supramolecular preparation of retinol and derivatives thereof provided in the present disclosure greatly reduces irritation while having obvious anti-wrinkle effect, so that the retinol and derivatives thereof simultaneously have mildness and high efficiency.

To sum up, the supramolecular preparation of retinol and derivatives thereof prepared in the present disclosure has a stable structure and stable property, which solves the problems of stability and irritation in the application of retinol and derivatives thereof, improves both the light and thermal stabilities of the supramolecular retinol and derivatives thereof, is not easy to be discolored or deactivated, avoids the irritation problems such as redness and swelling, hot pain and desquamation of skin caused by high concentrations of retinol and derivatives thereof, and can have ideal anti-wrinkle effect while keeping mildness.

The above-mentioned are merely for preferred embodiments of the present disclosure and not intended to limit the present disclosure. For one skilled in the art, various modifications and variations may be made to the present disclosure. Any amendments, equivalent replacements, improvements and so on made within the spirit and principle of the present disclosure should be covered within the scope of protection of the present disclosure.

INDUSTRIAL APPLICABILITY

The supramolecular preparation of retinol and derivatives thereof prepared in the present disclosure has a stable structure and stable property, which solves the problems of stability and irritation in the application of retinol and derivatives thereof, improves both the light and thermal stabilities of the supramolecular retinol and derivatives thereof, is not easy to be discolored or deactivated, avoids the irritation problems such as redness and swelling, hot pain and desquamation of skin caused by high concentrations of retinol and derivatives thereof, and can have ideal anti-wrinkle effect while keeping mildness.

What is claimed is:

1. A supramolecular preparation of retinol and derivatives thereof, comprising:
   3.00-25.0% of retinol and derivatives thereof;
   36.5-91.0% of hydroxypropyl γ-cyclodextrin;
   4.00-32.0% of hydroxypropyl methylcellulose stearoxy ether; and
   2.00-8.0% of PEG/PPG/polybutylene glycol-8/5/3 glycerin,
   wherein,
   the percentage is by mass; and
   a mass ratio of the PEG/PPG/polybutylene glycol-8/5/3 glycerin to the hydroxypropyl methylcellulose stearoxy ether is 1:2-4.

2. The supramolecular preparation of retinol and derivatives thereof according to claim 1, wherein the retinol and derivatives thereof comprise at least one selected from the group consisting of retinol, retinyl propionate, retinyl retinoate, retinyl linoleate, retinyl acetate, retinyl palmitate, retinal and hydroxypinacolone retinoate.

3. The supramolecular preparation of retinol and derivatives thereof according to claim 1 comprising:
   5-20% of the retinol and derivatives thereof;
   50-80% of the hydroxypropyl γ-cyclodextrin;
   8.00-25.0% of the hydroxypropyl methylcellulose stearoxy ether; and
   3.00-7.0% of the PEG/PPG/polybutylene glycol-8/5/3 glycerin,
   wherein the percentage is by mass.

4. The supramolecular preparation of retinol and derivatives thereof according to claim 1 comprising:
   6-15% of the retinol and derivatives thereof;
   60-75% of the hydroxypropyl γ-cyclodextrin;
   10.00-20.0% of the hydroxypropyl methylcellulose stearoxy ether; and
   4.00-6.0% of the PEG/PPG/polybutylene glycol-8/5/3 glycerin,
   wherein the percentage is by mass.

5. The supramolecular preparation of retinol and derivatives thereof according to claim 1 comprising:
   8-12% of the retinol and derivatives thereof;
   65-72% of the hydroxypropyl γ-cyclodextrin;
   12.00-18.0% of hydroxypropyl methylcellulose stearoxy ether; and
   4.5-5.5% of PEG/PPG/polybutylene glycol-8/5/3 glycerin,
   wherein the percentage is by mass.

6. The supramolecular preparation of retinol and derivatives thereof according to claim 1 comprising:
   10% of the retinol and derivatives thereof;
   70% of the hydroxypropyl γ-cyclodextrin;
   15% of the hydroxypropyl methylcellulose stearoxy ether; and
   5% of the PEG/PPG/polybutylene glycol-8/5/3 glycerin,
   wherein the percentage is by mass.

7. The supramolecular preparation of retinol and derivatives thereof according to claim 1, wherein the mass ratio of the PEG/PPG/polybutylene glycol-8/5/3 glycerin to the hydroxypropyl methylcellulose stearoxy ether is 1:2.2-3.8.

8. The supramolecular preparation of retinol and derivatives thereof according to claim 1, wherein the mass ratio of the PEG/PPG/polybutylene glycol-8/5/3 glycerin to the hydroxypropyl methylcellulose stearoxy ether is 1:2.4-3.6.

9. The supramolecular preparation of retinol and derivatives thereof according to claim 1, wherein the mass ratio of the PEG/PPG/polybutylene glycol-8/5/3 glycerin to the hydroxypropyl methylcellulose stearoxy ether is 1:2.6-3.4.

10. The supramolecular preparation of retinol and derivatives thereof according to claim 1, wherein the mass ratio of the PEG/PPG/polybutylene glycol-8/5/3 glycerin to the hydroxypropyl methylcellulose stearoxy ether is 1:2.8-3.2.

11. The supramolecular preparation of retinol and derivatives thereof according to claim 1, wherein the mass ratio of the PEG/PPG/polybutylene glycol-8/5/3 glycerin to the hydroxypropyl methylcellulose stearoxy ether is 1:3.

12. A cosmetic composition comprising the supramolecular preparation of retinol and derivatives thereof according to claim 1.

13. The cosmetic composition according to claim 12, wherein the cosmetic composition is an emollient, soothing oil, lotion cream, day cream, night cream, eye cream, UV protection product, anti-wrinkle product, gel, mask, balm, powder or sunscreen product.

14. A method for preparing a supramolecular preparation of retinol and derivatives thereof, comprising following steps:
   A. weighing, in percentage by mass, 3.00-25.0% of retinol and derivatives thereof, 36.5-91.0% of hydroxypropyl γ-cyclodextrin, 4.00-32.0% of hydroxypropyl methylcellulose stearoxy ether, and 2.00-8.0% of PEG/PPG/polybutylene glycol-8/5/3 glycerin, wherein a mass ratio of the PEG/PPG/polybutylene glycol-8/5/3 glycerin to the hydroxypropyl methylcellulose stearoxy ether is 1:2-4;
   B. weighing an appropriate amount of deionized water, mixing the hydroxypropyl γ-cyclodextrin and the deionized water in a mass ratio of 1:3, and stirring them with an agitator at a rotational speed of 500-800 rpm until the hydroxypropyl γ-cyclodextrin is completely dissolved to obtain an aqueous hydroxypropyl γ-cyclodextrin solution;
   C. weighing an appropriate amount of ethanol, dissolving the retinol and derivatives thereof in the ethanol in a mass ratio of 1:2-10, mixing them uniformly, and afterwards adding them dropwise into the aqueous hydroxypropyl γ-cyclodextrin solution obtained in step B at a rate of 5-20 ml per minute, and meanwhile keeping stirring the aqueous hydroxypropyl γ-cyclodextrin solution at a rotational speed of 500-800 rpm to obtain a mixed solution;

D. adding PEG/PPG/polybutylene glycol-8/5/3 glycerin and hydroxypropyl methylcellulose stearoxy ether in sequence to the mixed solution obtained in step C, and stirring them uniformly, and afterwards loading them in a sand mill to perform cyclical milling for 10-20 times, wherein a rotational speed is controlled at 3000-3500 rpm, and a temperature is not higher than 40° C., to obtain a pre-prepared liquid after completing the milling; and E. spray-drying the pre-prepared liquid obtained in step D under nitrogen protection using a spray dryer, wherein an air inlet temperature is controlled at 100-120° C., and a feed rate is controlled at 10-20 mL/min, and collecting a spray-dried product, to obtain the supramolecular preparation of retinol and derivatives thereof.

15. The supramolecular preparation of retinol and derivatives thereof according to claim 2, comprising:
    5-20% of the retinol and derivatives thereof;
    50-80% of the hydroxypropyl γ-cyclodextrin;
    8.00-25.0% of the hydroxypropyl methylcellulose stearoxy ether; and
    3.00-7.0% of the PEG/PPG/polybutylene glycol-8/5/3 glycerin,
    wherein the percentage is by mass.

16. The supramolecular preparation of retinol and derivatives thereof according to claim 2, comprising:
    6-15% of the retinol and derivatives thereof;
    60-75% of the hydroxypropyl γ-cyclodextrin;
    10.00-20.0% of the hydroxypropyl methylcellulose stearoxy ether; and
    4.00-6.0% of the PEG/PPG/polybutylene glycol-8/5/3 glycerin,
    wherein the percentage is by mass.

17. The supramolecular preparation of retinol and derivatives thereof according to claim 2, comprising:
    8-12% of the retinol and derivatives thereof;
    65-72% of the hydroxypropyl γ-cyclodextrin;
    12.00-18.0% of hydroxypropyl methylcellulose stearoxy ether; and
    4.5-5.5% of PEG/PPG/polybutylene glycol-8/5/3 glycerin,
    wherein the percentage is by mass.

18. The supramolecular preparation of retinol and derivatives thereof according to claim 2, comprising:
    10% of the retinol and derivatives thereof;
    70% of the hydroxypropyl γ-cyclodextrin;
    15% of the hydroxypropyl methylcellulose stearoxy ether; and
    5% of the PEG/PPG/polybutylene glycol-8/5/3 glycerin,
    wherein the percentage is by mass.

19. The supramolecular preparation of retinol and derivatives thereof according to claim 2, wherein the mass ratio of the PEG/PPG/polybutylene glycol-8/5/3 glycerin to the hydroxypropyl methylcellulose stearoxy ether is 1:2.2-3.8.

20. The supramolecular preparation of retinol and derivatives thereof according to claim 2, wherein the mass ratio of the PEG/PPG/polybutylene glycol-8/5/3 glycerin to the hydroxypropyl methylcellulose stearoxy ether is 1:2.4-3.6.

* * * * *